US010456535B2

(12) United States Patent
Hemy et al.

(10) Patent No.: US 10,456,535 B2
(45) Date of Patent: Oct. 29, 2019

(54) DRY POWDER INHALER

(71) Applicant: Presspart Manufacturing Ltd., Blackburn (GB)

(72) Inventors: Julian Hemy, Warrington (GB); Richard Turner, Simonstone (GB); Hans-Peter Schmelzer, Meerbusch (DE); Dietmar Schmitz, Brilon (DE); Stefan Hoffmann, Tönisvorst (DE); Ameet Sule, Maharashtra (IN); Sunita Sule, Maharashtra (IN); Matthias Seiler, Düsseldorf (DE); George Alexander Bostock, Cambridge (GB); Aki Hannu Einari Laakso, Cambridge (GB); Michael Worth, Cambridge (GB); Matthew Schumann, Cambridge (GB)

(73) Assignee: Presspart Manufacturing Ltd., Lancashire, Blackburn (GB)

( * ) Notice: Subject to any disclaimer, the term of this patent is extended or adjusted under 35 U.S.C. 154(b) by 443 days.

(21) Appl. No.: 15/484,232

(22) Filed: Apr. 11, 2017

(65) Prior Publication Data
US 2017/0333646 A1 Nov. 23, 2017

(30) Foreign Application Priority Data

May 23, 2016 (EP) .................................... 16170932

(51) Int. Cl.
*A61M 15/00* (2006.01)
*A61M 11/00* (2006.01)
(52) U.S. Cl.
CPC ........ *A61M 15/0005* (2014.02); *A61M 11/00* (2013.01); *A61M 15/0021* (2014.02);
(Continued)

(58) Field of Classification Search
CPC ............ A61M 11/00; A61M 2202/064; A61M 2206/16; A61M 15/00; A61M 15/0001;
(Continued)

(56) References Cited

U.S. PATENT DOCUMENTS 5,787,881 A * 8/1998 Chawla ............. A61M 15/0028
128/203.15
6,273,086 B1 * 8/2001 Ohki ................. A61M 15/0028
128/203.12

(Continued)

FOREIGN PATENT DOCUMENTS

WO 2011020554 A1 2/2011
WO 2013016787 A1 2/2011

(Continued)

OTHER PUBLICATIONS

Srinivas R. B. Behara et al; "Development of a High Efficiency Dry Powder Inhaler: Effects of Capsule Chamber Design and Inhaler Surface Modifications", Pharmaceutical Research, vol. 31; No. 2, (Feb. 1, 2014), pp. 360-372.

*Primary Examiner* — Joseph D. Boecker
(74) *Attorney, Agent, or Firm* — Carmody Torrance Sandak & Hennessey LLP

(57) ABSTRACT

The present invention relates to an inhaler device for delivering a dose of medicament in dry powder form from a container to a patient in need thereof. The inhaler comprises a swirl chamber in which particles of the medicament entrained in an airflow swirl upon inhalation thereby breaking up the agglomerates into finest dispersed powder.

14 Claims, 2 Drawing Sheets

(52) U.S. Cl.
CPC ... *A61M 15/0041* (2014.02); *A61M 2202/064* (2013.01); *A61M 2206/16* (2013.01)

(58) Field of Classification Search
CPC .......... A61M 15/0005; A61M 15/0008; A61M 15/00021; A61M 15/0028; A61M 15/003; A61M 15/0033; A61M 15/0035; A61M 15/0036; A61M 15/0038; A61M 15/004; A61M 15/0041; A61M 15/0091; A61M 15/0093; A61M 15/06

See application file for complete search history.

(56) References Cited

U.S. PATENT DOCUMENTS

| | | | |
|---|---|---|---|
| 6,371,111 B1 * | 4/2002 | Ohki | A61M 15/0028 128/203.12 |
| 2016/0158470 A1 * | 6/2016 | Esteve | A61M 15/0025 128/203.15 |
| 2016/0346488 A1 * | 12/2016 | Beller | A61M 15/0041 |
| 2016/0346490 A1 * | 12/2016 | Beller | A61M 15/0041 |
| 2017/0106154 A1 * | 4/2017 | Herder | A61M 15/0028 |
| 2018/0264208 A1 * | 9/2018 | Hemy | A61M 11/002 |

FOREIGN PATENT DOCUMENTS

| | | | | |
|---|---|---|---|---|
| WO | 2015006838 A1 | 1/2015 | | |
| WO | WO-2015110832 A1 * | 7/2015 | .......... | A61M 15/003 |

* cited by examiner

DRY POWDER INHALER

The present invention relates to an inhaler device for delivering a dose of medicament in dry powder form from a container to a patient in need thereof.

BACKGROUND OF THE INVENTION

Inhalers are commonly used to deliver drugs into the lung of a patient in need thereof. Different types of inhalers have been developed and are available on the market, amongst which dry powder inhalers (DPIs) are becoming attractive in the treatment of various respiratory problems such as asthma, bronchitis or chronic obstructive pulmonary disease (COPD) and for the delivery of non-asthma drugs delivered via inhalation.

In dry powder inhalers, the dose of medicament is present in dry powder form and usually pre-packed in a capsule. Blister-based dry powder inhalers are also known.

In capsule-based dry powder inhalers, a capsule is placed into a capsule chamber of the inhaler before inhalation and opened, e.g. by piercing the capsule at its ends. Subsequently, the patient inhales through a nosepiece or mouthpiece whereupon an inhalation airflow is generated within the inhaler. The medicament in dry powder form is released from the capsule, entrained into the inhalation airflow and inhaled by the patient.

For dose consistency, it is desirable that as much as possible of the dose of medicament is released from the capsule, inhaled by the patient and delivered to the site of action in the lung. Moreover it is desirable to break down the particle size of the medicament in dry powder form contained in the capsule in order to enable a good absorption of the medicament in the lung.

Medicaments in dry powder form contained in capsules usually consist of a blend of the active ingredient and a bulking agent, e.g. lactose. The powder blend is usually present in form of big agglomerates which are usually a mixture of big and small particles. However, big agglomerates often show a poor release from the capsule and/or a poor lung uptake. Thus, in conventional dry powder inhalers it is desired to break and/or de-agglomerate larger particles into smaller, breathable particles prior or during inhalation in order to allow for an efficient release from the capsule as well as an efficient lung uptake. Particles with a size of not more than 5 μm are believed to be particularly advantageous for an efficient lung uptake.

One approach of breaking down/de-aggregate big agglomerates inside the capsule during inhalation is to set the capsule into motion thereupon causing impacts between the capsule and the capsule chamber, whereby stronger impacts are believed to lead to a better breakdown of the powder particles and consequently to a more efficient release from the capsule.

Pending European Patent Application No. 15191215.1 describes an improved dry powder inhaler for delivering a dose of medicament in dry powder form from a container to a patient in need thereof. The inhaler comprises first and second airflow paths which are arranged such that during inhalation, a capsule having a longitudinal axis and first and second end sections delimiting the capsule on opposing ends located in the capsule chamber performs an oscillating movement in the capsule chamber parallel to its longitudinal axis between first and the second sidewall portions of the capsule chamber. The particles of the medicament inhaled by the patient are too large to enable an optimal absorption in the lung of the patient.

It is an object of the present invention to provide an inhaler device that overcomes the problems associated with the devices of the prior art, and further improves the airflow of the device. In particular, it is an object of the present invention to provide an inhaler device that improves the deagglomeration of the particles in which the medicament is contained.

SUMMARY OF THE INVENTION

The above mentioned objects are achieved by an inhaler device comprising an inhaler housing comprising at least one air inlet duct. The inhaler device further comprises an elongated capsule chamber adapted for receiving a capsule which contains a dose of medicament in dry powder form. The capsule chamber has a longitudinal axis and is defined by a wall arrangement including a first and a second supporting wall portion opposing each other in a direction perpendicular to the longitudinal axis of the capsule chamber. The wall arrangement further includes first and second sidewall portions opposing each other in the direction of the longitudinal axis of the capsule chamber.

The inhaler device further comprises a mouthpiece portion through which the medicament in dry powder form is dispensable and at least first and second airflow paths which extend between the at least one air inlet duct, the capsule chamber and the mouthpiece portion to enable an inhalation airflow formed upon inhalation to flow through the at least one air inlet duct via the capsule chamber and the mouthpiece portion such that the dose of medicament is entrained in air and dispensed through the mouthpiece portion. The first airflow path comprises at least a first intermediate duct extending from the at least one air inlet duct to a first capsule chamber inlet adjacent to the first sidewall portion, and at least a first outlet duct extending from a first capsule chamber outlet adjacent to the first sidewall portion in direction to the mouthpiece portion. The second airflow path comprises at least a second intermediate duct extending from the at least one air inlet duct to a second capsule chamber inlet adjacent to the second sidewall portion, and at least a second outlet duct extending from a second capsule chamber outlet adjacent to the second sidewall portion in direction to the mouthpiece portion. The at least first and second outlet ducts extend, upon exit from the capsule chamber, towards a swirl chamber and are connected to it. The swirl chamber comprises a base from which an inner wall surrounding that base vertically extends towards a swirl chamber outlet. The swirl chamber outlet is connected to the mouthpiece portion and encloses a flow cross-section area which is smaller than an area of the base surrounded by the inner wall.

The tapering of the swirl chamber from the base towards the swirl chamber outlet may be achieved for example by a conical shape of the swirl chamber or by the inner wall extending from the base along a vertical axis followed by a rounding of the inner wall towards said vertical axis.

The at least first and second outlet ducts extend, upon exit from the capsule chamber, towards a swirl chamber such that upon inhalation a flow is introduced into the swirl chamber which has a component of velocity in a tangential direction to the swirl chamber such that a swirl arises in the swirl chamber.

Preferably the at least first and second outlet ducts extend, upon exit from the capsule chamber, towards a swirl chamber in a helix shaped manner. Depending on the direction the helix is twisted the swirl in the swirl chamber turns clockwise or counter clockwise. The swirl flows along the inner wall of the swirl chamber spiraliform from the outlet ducts towards the swirl chamber outlet. The incline of the helix shape substantially influences the incline of the airflow within the swirl chamber. Being drawn into that swirl the agglomerates break up by colliding with each other and the inner wall. It is to be understood that the outlet ducts do not need to be strictly helical or spiralling, as long as they drive rotating flow in the swirl chamber.

According to an alternative embodiment the at least first and second outlet ducts that extend towards the swirl chamber converge, spiralling inwards, or diverge, spiralling outwards from a vertical axis along which the inner wall extends from the base.

In a preferred embodiment the first and second outlet ducts are fed into the swirl chamber substantially parallel to the inner wall. According to the present invention the term "parallel" is to be understood such that the outlet ducts are positioned parallel to a tangent drawn on a virtually outer side of the inner wall. In case the inner wall has a polygon shape the term "parallel" is to be understood that each outlet duct is positioned parallel to one of the inner surfaces extending vertically between the edges of the polygon shape.

As the outlet ducts are feed substantially parallel to the inner wall there is a smooth transition between the outlet ducts and the swirl chamber.

In an alternative embodiment the first and second outlet ducts are fed into the swirl chamber through the base adjacent to the inner wall. Preferably the base comprises swirl chamber openings through which the outlet ducts are connected to the swirl chamber. Thus, the whole vertical extend of the swirl chamber is used for the swirl to break down the agglomerates the medicament is contained in. As the outlet ducts are positioned adjacent to the inner wall all of the flow energy of the airflow substantially contributes to the generation of the swirl.

Preferably the swirl chamber comprises a dome like shape having a top, at which the swirl chamber outlet is located. Because of the conservation of the angular momentum the tangential velocity of the swirl increases when the inner wall of the swirl chamber tapers towards the swirl chamber outlet. Consequently as the swirl approaches the swirl chamber outlet the angular velocity increases thereby intensifying the swirl and the breakdown of the agglomerates. This results in shear forces on the agglomerates within the flow, helping to break them up. The dome shape therefore contributes to a more efficient break down of the agglomerates the medicament is contained in.

Advantageously the swirl chamber is rotationally symmetrical to a vertical axis along which the inner wall extends from the base. The rotationally symmetrical shape reduces the flow losses to a minimum.

According to an alternative embodiment the inner wall forms a polygon surrounding the base. The polygon shape improves the breakdown of the particles the medicament is contained in as they continuously collide with the inner wall on their way towards the swirl chamber outlet.

Advantageously the mouthpiece portion comprises a mouthpiece duct which extends from the swirl chamber to a mouthpiece dispensing opening. Preferably the mouthpiece duct is cylindrical.

According to an alternative embodiment a mesh is positioned in the mouthpiece duct, wherein the mesh extends perpendicular to a flow direction of the airflow. The mesh is used to reduce the swirl in the airflow in order to improve inhalation of the medicament. Preferably the mesh is located in or adjacent to the swirl chamber outlet. Additionally the maximum size of particles the medicament is contained in being dispensed through the mouthpiece dispensing opening can be defined by the size of the through holes in the mesh.

Preferably at least one plate is positioned in the mouthpiece duct, wherein the plate extends in flow direction of the airflow. The plate reduces the swirl in the airflow.

Also preferred is a cross formed by two plates arranged perpendicular to each other which is positioned in the mouthpiece duct, wherein the plates extend in flow direction of the airflow. The cross further reduces the swirl in the airflow.

Alternatively the first and second airflow paths are arranged such that during inhalation, a capsule having a longitudinal axis and first and second end sections delimiting the capsule on opposing ends located in the capsule chamber performs an oscillating movement in the capsule chamber parallel to the longitudinal axis of the capsule between the first and the second sidewall portions when an airflow is initiated through the at least first and the second airflow paths in a direction from the at least one air inlet duct towards the mouthpiece portion. Preferably, while performing the oscillating movement, impacts between the capsule, in particular between its first and second end sections, and the first and second sidewall portions of the capsule chamber are generated such that a dose of medicament in dry powder form contained within the capsule is broken down into fine, breathable particles and finely dispersed inside the capsule, whereupon the fine particles are released into the airstream.

Preferably, the capsule containing a dose of medicament in dry powder form comprises a central section between said first and second end sections. Preferably, the central section is in cylindrical form. The central section of the capsule is preferably adapted to be supported by the first and second supporting wall portions against a movement in a plane extending perpendicular to the longitudinal axis. According to this embodiment, after being inserted into the capsule chamber, the capsule moves only parallel to its longitudinal axis between the first and second sidewall portions and/or rotates around its longitudinal axis.

According to a preferred embodiment the inhaler device comprises a moveable piercing means located in the first and second sidewall portions of the capsule chamber for piercing a capsule located in the capsule chamber at its first and second end sections. Alternatively, the capsule may be opened by cutting means.

BRIEF DESCRIPTION OF THE DRAWINGS

The invention is further described by referring to the appended figures which show preferred embodiments and shall by no means limit the present invention.

DETAILED DESCRIPTION OF THE INVENTION

Figure 1:
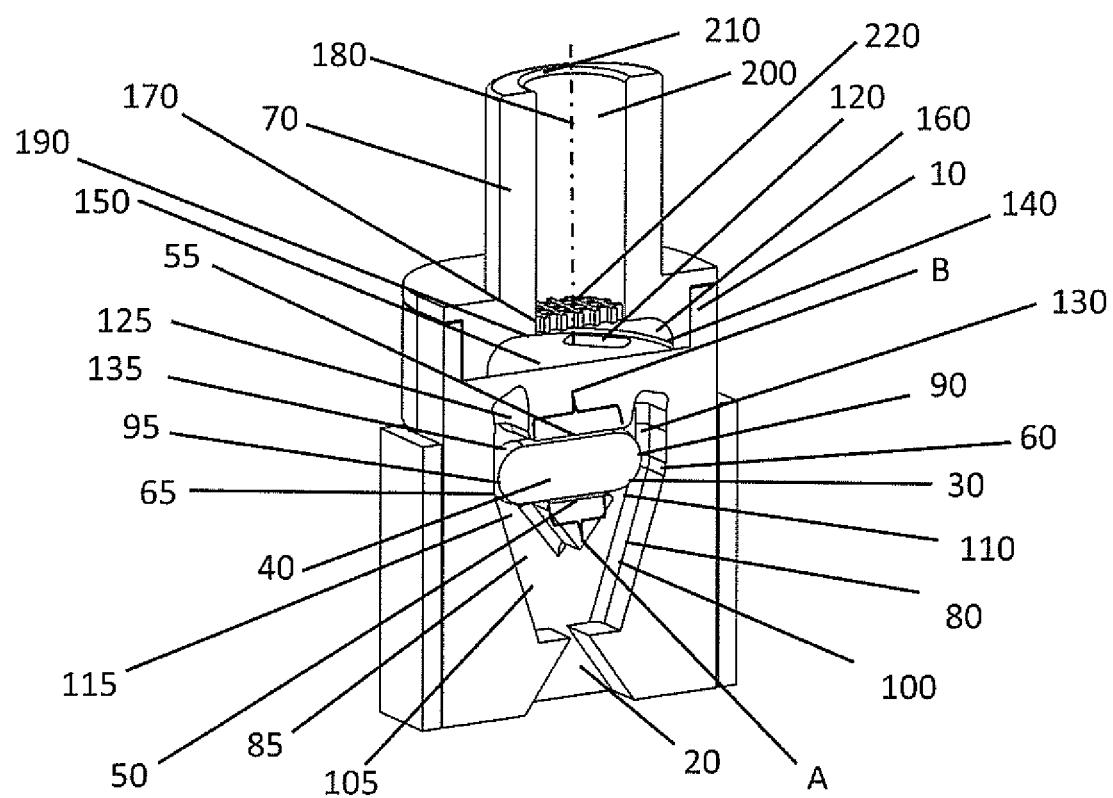
FIG. 1 shows a cross sectional view of an inhaler according to the present invention together with a capsule inserted in the capsule chamber.
Figure 2:
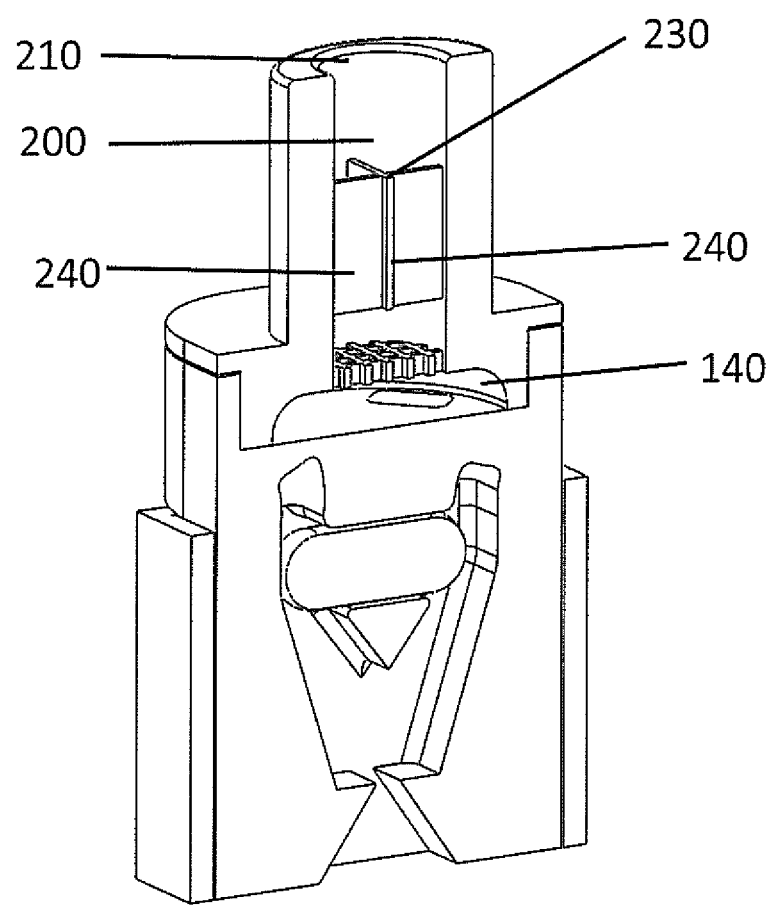
FIG. 2 shows a cross sectional view of another embodiment of an inhaler according to the present invention.

With reference to FIG. 1, a first exemplary embodiment of an inhaler device according to the present invention will be described.

The inhaler device comprises an inhaler housing 10 having one air inlet duct 20 through which ambient air flows into the inhaler device during inhalation. The inhaler further comprises an elongated capsule chamber 30 adapted for receiving a capsule 40 containing a dose of medicament in dry powder form. FIG. 1 shows an embodiment of the inventive inhaler device together with a capsule 40 inserted in the capsule chamber 30. The capsule 40 has a longitudinal axis and first and second end sections 90, 95 delimiting the capsule 40 on opposing ends. The capsule 40 further comprises a central, cylindrical section between said first and second end sections 90, 95.

The capsule chamber 30 has a longitudinal axis and is defined by a wall arrangement including a first and a second supporting wall portion 50, 55 opposing each other in a direction perpendicular to the longitudinal axis. As shown in FIG. 1, first and second supporting wall portions 50, 55 are arranged parallel to each other. The first supporting wall portion 50 has an extension in a direction extending parallel to the longitudinal axis of the capsule chamber 30 with a length "A" and the second supporting wall portion 55 has an extension in a direction extending parallel to the longitudinal axis of the capsule chamber 30 with a length "B". In the embodiment shown in FIG. 1, "B" is larger than "A".

The wall arrangement further includes first and second sidewall portions 60, 65 opposing each other in the direction of the longitudinal axis of the capsule chamber 30.

The inhaler device further comprises a swirl chamber 140 in which the air upon exit from the capsule chamber 30 swirls. Adjacent to the swirl chamber 140 there is a mouthpiece portion 70 through which the medicament in dry powder form is dispensable.

Moreover, the embodiment of the inventive inhaler device shown in FIG. 1 comprises at least first and second airflow paths 80, 85 which extend between the at least one air inlet duct 20, the capsule chamber 30 and the mouthpiece portion 70 to enable an inhalation airflow formed upon inhalation to flow through the air inlet duct 20 via the capsule chamber 30, the swirl chamber 140 and the mouthpiece portion 70.

The first airflow path 80 comprises a first intermediate duct 100 extending from the one air inlet duct 20 to a first capsule chamber inlet 110 adjacent to the first sidewall portion 60 and a first outlet duct 120 extending from a first capsule chamber outlet 130 adjacent to the first sidewall portion 60 in direction to the mouthpiece portion 70. The second airflow path 85 comprises a second intermediate duct 105 extending from the air inlet duct 20 to a second capsule chamber inlet 115 adjacent to the second sidewall portion 65, and a second outlet duct 125 extending from a second capsule chamber outlet 135 adjacent to the second sidewall portion 65 in direction to the mouthpiece portion 70.

The first capsule chamber inlet 110 is formed between the first supporting wall portion 50 and the first sidewall portion 60. The second capsule chamber inlet 115 is formed between the first supporting wall portion 50 and the second sidewall portion 65. The first capsule chamber outlet 130 is formed between the second supporting wall portion 55 and the first sidewall portion 60. The second capsule chamber outlet 135 is formed between the second supporting wall portion 55 and the second sidewall portion 65.

In the embodiment shown in FIG. 1, the size of the first capsule chamber inlet 110 is identical to the size of the second capsule chamber inlet 115 and the size of the first capsule chamber outlet 130 is identical to the size of the second capsule chamber outlet 135. The size of said first and second capsule chamber inlets 110, 115 is larger than the size of said first and second capsule chamber outlets 130, 135.

The first and second intermediate ducts 100, 105 taper in direction from the at least one air inlet duct 20 to the first and second capsule chamber inlets 110, 115 such that air flowing from the at least one air inlet duct 20 to the capsule chamber 30 is accelerated when flowing through first and second intermediate ducts 100, 105.

The first and second outlet ducts 120, 125 extend from the first and second capsule chamber outlets 130, 135 towards the swirl chamber 140 in a helix shaped manner and are connected to it. The swirl chamber 140 comprises a base 150 from which an inner wall 160 surrounding that base 150 vertically extends towards a swirl chamber outlet 170. The swirl chamber outlet 170 is connected to the mouthpiece portion 70 and encloses a flow cross-section area which is smaller than an area of the base surrounded by the inner wall 160.

The swirl chamber 140 is rotationally symmetrical to a vertical axis 180 along which the inner wall 160 extends from the base 150. The swirl chamber 30 comprises a dome like shape having a top 190, at which the swirl chamber outlet 170 is located. It is to be understood that the inner wall 160 may also form a polygon surrounding the base 150 such as for example a hexagon or an octagon.

The first and second outlet ducts 120, 125 are fed into the swirl chamber 140 through the base substantially parallel and adjacent to the inner wall 160. The incline of the outlet ducts 120, 125 substantially influences the incline of the air swirling upon inhalation counterclockwise along the inner wall 160 of the swirl chamber 30 spiraliform towards the mouthpiece portion 70.

The mouthpiece portion 70 comprises a cylindrical mouthpiece duct 200 which extends from the swirl chamber 30 to a mouthpiece dispensing opening 210. A mesh 220 is positioned in the mouthpiece duct 200 and extends perpendicular to a flow direction of the airflow.

The capsule 40 inserted into the capsule chamber 30 has an extension between its first and second end sections 90, 95 that is larger than the size of the first and second capsule chamber inlets 110. In particular, the capsule 40 inserted into the capsule chamber 30 has an extension between its first and second end sections that is larger than the sum of length "B" and the size of the first or second capsule chamber outlet 130, 135. In this way, the capsule 40 acts as an airflow barrier preventing air to flow from the first airflow path 80 to the second airflow path 85 (or vice versa) within the capsule chamber 30. Additionally, a constriction zone is created within the capsule chamber 30 between the first or second sidewall portion 60, 65 and the first or second end section 90, 95 of the capsule 40. FIG. 1 shows a situation where the capsule 40 blocks the second airflow path 85 and creates a constriction zone between the first end section 90 of the capsule 40 and the first sidewall portion 60.

Furthermore, the embodiment shown in FIG. 1 comprises an air inlet duct 20 that abruptly expands prior to its connection with the at least first and second airflow paths 80, 85.

During inhalation, an inhalation airflow is formed within the inhaler device. The inhalation airflow forms an air stream into a larger space upon exiting the air inlet duct 20. As the second airflow path 85 is blocked by the capsule 40, said air stream flows into the first airflow path 80. According to the principle of continuity, the inhalation airflow has an increased velocity when flowing through the constriction zone formed between the first end section 90 of the capsule 40 and the first sidewall portion 60. According to the principle of conservation of mechanical energy, said gain in kinetic energy—due to the increased velocity of the air flowing through the constriction zone—leads to a drop in pressure in the capsule chamber 30 at the proximity of the first sidewall portion 60 (Venturi effect). Consequently, due to the reduced pressure in the capsule chamber 30 at the proximity of the first sidewall portion 60, the capsule 40 is moved towards the first sidewall portion 60. Subsequently, after being moved to the first sidewall portion 60, the capsule 40 blocks the first airflow path 80. At the same time, the second airflow path 85 is opened. The capsule 40 now forms a constriction zone within the capsule chamber 30 between the second end section 95 of the capsule 40 and the second sidewall portion 65. Now, as the first airflow path 80 is blocked by the capsule 40, the inhalation airflow streams into the second airflow path 85 thereby creating a reduced pressure inside the capsule chamber 30 when flowing through the constriction zone. Thus, the capsule is moved to the second sidewall portion 65 thereby (re-) opening the first airflow path 80 and (re-)closing the second airflow path 85. In this way, the capsule 40 performs an oscillating movement in the capsule chamber 30 parallel to its longitudinal axis between the first and second sidewall portions 60, 65 when an airflow is initiated through the first and the second airflow paths 80, 85 in a direction from the air inlet duct 20 towards the mouthpiece portion 70. While performing the oscillating movement, impacts between the capsule 40, in particular its first and second end sections 90, 95, and the first and second sidewall portions 60, 65 of the capsule chamber 30 are generated such that a dose of medicament in dry powder form contained within the capsule 40 is broken down into fine, breathable fractions and finely dispersed inside the capsule 40.

The finely dispersed powder exits the capsule 40 through holes in the first and second end sections 90, 95, and is entrained in the inhalation airflow flowing through the outlet ducts 120, 125 into the swirl chamber 140. The holes may be pierced using movable piercing means (not shown). Preferably, said moveable piercing means are located in the first and second sidewalls 60, 65 of the capsule chamber 30.

Due to the helix shaped run of the first and second outlet ducts 120, 125 the airflow enters the swirl chamber 140 substantially parallel to the inner wall 160. The airflow swirls along the inner wall 160 counterclockwise towards the swirl chamber outlet 170. Particles within the finely dispersed powder hit the inner wall 160 and collide with each other while swirling, thereby being broken up.

Due to the conservation of the angular momentum the angular velocity of the airflow increases as soon as it approaches the tapering of the dome like shaped swirl chamber 140. This intensifies the swirl as well as the breakdown of the particles and results in a finest dispersed powder entrained in the airflow. Said airflow exits the swirl chamber 140 through the swirl chamber outlet 170 thereby passing the mesh 220 located in the mouthpiece duct 200. The mesh 220 is adapted to reduce the swirl in the airflow in order to improve inhalation of the medicament. Furthermore the mesh 220 may block particles which exceed a predefined size that do not fit through the mesh pattern. The medicament entrained in the airflow is then dispensed over the mouthpiece dispensing opening 210 into a lung of a patient in need thereof.

FIG. 2 shows a second embodiment of the inhaler device according to the present invention.

The inhaler device differs from the one shown in FIG. 1 by a cross 230 positioned in the mouthpiece duct 200. The cross 230 is formed by two plates 240 arranged perpendicular to each other, wherein the plates 240 extend in flow direction of the airflow through the mouthpiece duct 200. The cross 230 further reduces the swirl of the airflow exiting the swirl chamber 140 such that the airflow is dispensed from the mouthpiece dispensing opening 210 substantially laminar. The cross 230 may be used in combination with the mesh 220 (FIG. 1) or as a sole swirl reducing means.

The invention claimed is:

1. An inhaler device comprising an inhaler housing comprising at least one air inlet duct;

an elongated capsule chamber adapted for receiving a capsule which contains a dose of medicament in dry powder form, and wherein the capsule chamber has a longitudinal axis and is defined by a wall arrangement including a first and a second supporting wall portion opposing each other in a direction perpendicular to the longitudinal axis and first and second sidewall portions opposing each other in the direction of the longitudinal axis;

a mouthpiece portion through which the medicament in dry powder form is dispensable; and at least first and second airflow paths which each extend between the at least one air inlet duct, the capsule chamber and the mouthpiece portion to enable an inhalation airflow formed upon inhalation to flow through the at least one air inlet duct via the capsule chamber and the mouthpiece portion such that the dose of medicament is entrained in air and dispensed through the mouthpiece portion;

wherein the first airflow path comprises at least a first intermediate duct extending from the at least one air inlet duct to a first capsule chamber inlet adjacent to the first sidewall portion, and at least a first outlet duct extending from a first capsule chamber outlet adjacent to the first sidewall portion in direction to the mouthpiece portion; and the second airflow path comprises at least a second intermediate duct extending from the at least one air inlet duct to a second capsule chamber inlet adjacent to the second sidewall portion, and at least a second outlet duct extending from a second capsule chamber outlet adjacent to the second sidewall portion in direction to the mouthpiece portion, wherein the at least first and second outlet ducts extend, upon exit from the capsule chamber, towards a swirl chamber and are connected to it, wherein said swirl chamber comprises a base from which an inner wall surrounding that base vertically extends towards a swirl chamber outlet and, wherein the swirl chamber outlet is connected to the mouthpiece portion and encloses a flow cross-section area which is smaller than an area of the base surrounded by the inner wall.

2. An inhaler device according to claim 1, wherein the at least first and second outlet ducts extend, upon exit from the capsule chamber, towards the swirl chamber in a helix shaped manner.

3. An inhaler device according to claim 1, wherein the at least first and second outlet ducts that extend towards the swirl chamber converge, spiraling inwards, or diverge, spiraling outwards from a vertical axis (180) along which the inner wall extends from the base.

4. An inhaler device according to claim 1, wherein the first and second outlet ducts are fed into the swirl chamber substantially parallel to the inner wall.

5. An inhaler device according to claim 1, wherein the first and second outlet ducts are fed into the swirl chamber through the base adjacent to the inner wall.

6. An inhaler device according to claim 1, wherein the swirl chamber comprises a dome like shape having a top, at which the swirl chamber outlet is located.

7. An inhaler device according to claim 1, wherein the swirl chamber is rotationally symmetrical to a vertical axis along which the inner wall extends from the base.

8. An inhaler device according to claim 1, wherein the inner wall forms a polygon surrounding the base.

9. An inhaler device according to claim 1, wherein the mouthpiece portion comprises a mouthpiece duct which extends from the swirl chamber to a mouthpiece dispensing opening.

10. An inhaler device according to claim 9, wherein a mesh is positioned in the mouthpiece duct, wherein the mesh extends perpendicular to a flow direction of the airflow.

11. An inhaler device according to claim 9, wherein at least one plate is positioned in the mouthpiece duct, wherein the plate extends in flow direction of the airflow.

12. An inhaler device according to claim 9, wherein a cross formed by two plates arranged perpendicular to each other is positioned in the mouthpiece duct, wherein the plates extend in flow direction of the airflow.

13. An inhaler device according to claim 1, characterized in that the first and second airflow paths are arranged such that during inhalation, the capsule having a longitudinal axis and first and second end sections delimiting the capsule on opposing ends located in the capsule chamber performs an oscillating movement in the capsule chamber parallel to the longitudinal axis of the capsule between the first and the second sidewall portions when an airflow is initiated through the at least first and the second airflow paths in a direction from the at least one air inlet duct towards the mouthpiece portion.

14. The inhaler device according to claim 1, further comprising a moveable piercing means located in the first and second sidewall portions of the capsule chamber for piercing the capsule located in the capsule chamber at first and second end sections of the capsule.

* * * * *